United States Patent [19]

Wiezer

[11] 4,267,322
[45] May 12, 1981

[54] PROCESS FOR THE MANUFACTURE OF 7-NITRO-1,3,5-TRIAZA-ADAMANTANE

[75] Inventor: Hartmut Wiezer, Gersthofen, Fed. Rep. of Germany

[73] Assignee: Hoechst Aktiengesellschaft, Fed. Rep. of Germany

[21] Appl. No.: 57,566

[22] Filed: Jul. 16, 1979

[30] Foreign Application Priority Data

Jul. 19, 1978 [DE] Fed. Rep. of Germany ........ 2831632

[51] Int. Cl.³ .......................................... C07D 487/18
[52] U.S. Cl. ................................................... 544/180
[58] Field of Search ........................................ 544/180

[56] References Cited

U.S. PATENT DOCUMENTS 3,301,854  1/1967  Gabel ................................... 544/180
3,575,974  4/1971  Hodge ................................. 544/180

OTHER PUBLICATIONS

Safar et al., *Coll. Czech. Chem. Comm.*, vol. 40, pp. 2179–2182 (1957).

*Primary Examiner*—John M. Ford
*Attorney, Agent, or Firm*—Connolly and Hutz

[57] ABSTRACT

The invention relates to an improved process for the manufacture of 7-nitro-1,3,5-triaza-adamantane from hexamethylene tetramine and nitromethane, using alcohols or carboxylic acids as solvent the water content of which is not allowed to exceed a defined level. The product of the process is obtained with good yield and a high purity degree.

4 Claims, No Drawings

PROCESS FOR THE MANUFACTURE OF 7-NITRO-1,3,5-TRIAZA-ADAMANTANE

The invention relates to an improved process for the manufacture of 7-nitro-1,3,5-triaza-adamantane of the formula (I)

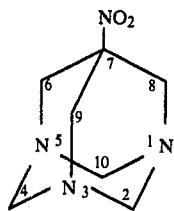

which is suitable for stabilizing plastic materials and which is simultaneously important as starting product for the synthesis of other stabilizers.

It is known that 7-nitro-1,3,5-triaza-adamantane can be prepared by reaction of paraformaldehyde with nitromethane and ammonium acetate in an alcoholic medium (U.S. Pat. No. 3,301,854). Another process consists in reacting tris-(hydroxymethyl)-nitromethane with aqueous ammonia and aqueous formaldehyde solution (E. B. Hodge, J.Chem.Soc. 37, 2 (1972), p. 320/321). A further process is known according to which hexamethylene triamine is reacted with nitromethane and formic acid in aqueous 80% ethanol at elevated temperature (M. Safar et al., Collection Czechoslov.Chem.Comm. 40 (1975), pp. 2179–2182).

In the process cited first, there are not obtained yields of from 70 to 77%, as indicated, but of from 45 to 55% only, which is stated by different authors in congruency with another (E. B. Hodge, loc.cit.; A. T. Nielsen, J. Heterocyclic Chem. 12, 1 (1975), pp. 161–164; A. R. Farminer et al., US NTIS AD-A Rep. 1975, No. 008097, p. 12). The yield of the process cited secondly is a mere 28%. The last-mentioned process is said to proceed with a yield of 65%; however, this yield comprises at least 20% of impurities which are extremely disturbing because they practically prevent processing by catalytic hydrogenation to 7-amino-1,3,5-triaza-adamantane due to contamination of the catalysts, as proved by Safar's hydrogenation results. For, it follows from the papers of Hodge, Farminer and Nielsen that, because of the drastically diverging melting point, the hydrogenation product obtained by Safar cannot be anything but a starting material. Therefore, the above three processes are unsuitable for the manufacture of 7-nitro-1,3,5-triaza-adamantane on an industrial scale.

It has now been found that 7-nitro-1,3,5-triaza-adamantane is obtained with a surprisingly high yield and an unexpected purity degree of carrying out the last-mentioned process according to a modified embodiment.

Subject to the present invention is therefore a process for the manufacture of 7-nitro-1,3,5-triaza-adamantane by reaction of hexamethylene tetramine with nitromethane in an organic solvent at elevated temperature in the presence of an acid catalyst, which comprises using as solvent an aliphatic alcohol having from 1 to 4 carbon atoms and a water content not exceeding 4 weight %, or an anhydrous aliphatic monocarboxylic acid having from 1 to 3 carbon atoms, employing the catalyst in an amount at least equimolar to that of the hexamethylene tetramine, and carrying out the reaction at 40° to 180° C.

It was not to be expected that hexamethylene tetramine could be reacted with nitromethane under acidic conditions without adding water, because it is known that in the process starting from hexamethylene tetramine the latter one is first converted with water and acids, for example formic acid, to ammonium formate and formaldehyde according to the following scheme:

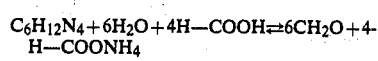

which products react only then with nitromethane in the manner as described by Hodge, Nielsen and Farminer (loc. cit.) to form nitro-aza-adamantane. The conversion according to the operation mode of the invention seems therefore to proceed according to an entirely different reaction mechanism.

Surprising is furthermore the high purity degree of the final product. It is precipitated from the reaction solution in the form of yellowish crystals which are just washed with water and which can be subjected then without any further purification operation to, for example, hydrogenation, in order to obtain the amino compound.

Hexamethylene tetramine and nitromethane are preferably used in an equimolar ratio; an excess of the one or the other component does not bring about any advantage.

Suitable organic solvents are preferably aliphatic mono- or di-alcohols having from 1 to 4 or 2 to 4 carbon atoms, especially methanol and ethanol, furthermore propanol, isopropanol, n-butanol, ethyleneglycol, propyleneglycol, or aliphatic monocarboxylic acids having from 1 to 3 carbon atoms, preferably acetic acid. It is decisive for a successful issue of the process that the solvents do not contain more than 4, preferably not more than 2, weight % of water, because the quality of the product decreases as the water content of the solvent increases, and by-products are formed which have a dark color and nearly cannot be eliminated. The amount of solvent is generally a 1- to 10-fold of the weight of the hexamethylene tetramine used.

By acid catalysts, there are to be understood protonic acids such as hydrochloric acid, organic sulfonic or phosphonic acids, and especially carboxylic acids, such as formic, acetic, propionic or p-toluenesulfonic acid. The catalysts are used in a 1- to 10-fold, preferably 1- to 5-fold, and especially 1 to 1.5-fold, molar amount, relative to the hexamethylene tetramine. When a carboxylic acid is used as solvent, the catalyst can of course be omitted; however, care has to be taken that an amount of this "acid solvent" is present which is at least equimolar to that of the hexamethylene tetramine.

The reaction is carried out at a temperature of from 40° to 180° C., preferably 60° to 140° C., and especially 80° to 130° C. A pressure of from 1 to about 20 bars establishes itself depending on the kind of solvent and the temperature chosen. The reaction time likewise depends on the temperature; generally, it is from 1 to 25 hours.

The following Examples illustrate the invention.

EXAMPLE 1

140 g (1 mol) of hexamethylene tetramine, 61 g (1 mol) of nitromethane and 200 g of glacial acetic acid are heated with agitation at 95° C. for 8 hours. After about 30 minutes, the reaction becomes exothermic, and the product begins to crystallize. After the reaction is complete, the product is suction-filtered and washed twice with 150 ml of water.

Yield: 127=69% of th.; yellowish crystals.

EXAMPLE 2

126 g of hexamethylene tetramine, 65 g of nitromethane, 150 g of butanol and 60 g of glacial acetic acid are refluxed for 4 hours. Subsequently, the precipitated crystals are suction-filtered and washed twice with 100 ml each of water.

Yield: 114 g=68% of th., relative to hexamethylene tetramine.

EXAMPLE 3

140 g (1 mol) of hexamethylene tetramine, 65 g of nitromethane and 150 g of glacial acetic acid are maintained for 4 hours at 95° C. The product is suction-filtered and washed twice with 150 ml each of water.

Yield: 129 g=70% of th.

EXAMPLE 4

70 g of hexamethylene tetramine, 30.5 g of nitromethane and 25 g of formic acid are refluxed for 20 hours in 250 ml of 96% ethanol. The solids precipitated are suction-filtered and washed with water.

Yield: 63.5 g=69% of th.

EXAMPLE 5

70 g of hexamethylene tetramine, 30.5 g of nitromethane and 60 g of glacial acetic acid are refluxed for 20 hours in 250 ml of 96% ethanol. The crystals precipitated are suction-filtered and washed with water.

Yield: 67.1 g=72.8% of th.

EXAMPLE 6

70 g of hexamethylene tetramine, 30.5 g of nitromethane and 30 g of glacial acetic acid are refluxed for 20 hours in 250 ml of absolute ethanol. The precipitated crystals are suction-filtered and washed with water.

Yield: 72.1 g=78.4% of th.

EXAMPLE 7

560 g of hexamethylene tetramine, 244 g of nitromethane and 400 g of glacial acetic acid are heated in a pressure vessel in 1300 g of anhydrous methanol, first for 20 hours at 80° C. and then for 30 minutes at 140° C. The precipitated solids are suction-filtered after cooling, washed twice with 500 ml of water and dried.

Yield: 515 g=70.0% of th.

EXAMPLE 8

70 g of hexamethylene tetramine, 45 g of glacial acetic acid and 30.5 g of nitromethane are heated for 5 hours at 100° C. in 250 ml of methanol in a pressure vessel. The precipitated solids are suction-filtered, washed with water and dried.

Yield: 67 g=72.8% of th.

EXAMPLE 9

70 g of hexamethylene tetramine, 30.5 g of nitromethane and 30 g of glacial acetic acid are heated for 3 hours at 110° C. with agitation.

66 g=71.7% of th. of the intended compound are obtained.

EXAMPLES 10 to 12

These examples prove that the water content of the solvent used has a considerable influence on the yield of product and its quality:

140 g of hexamethylene tetramine (1 mol), 61 g of nitromethane (1 mol) and 90 g of glacial acetic acid (1.5 mol) were refluxed for 22 hours in the presence of 400 g of ethanol containing different amounts of water. The product was suction-filtered in hot state and dried. The results are listed in the following Table. The solubility in water and the behavior on heating are a measure for the purity of the product.

| Ex. No. | Wt. % $H_2O$ in ethanol | Yield (%) | Aspect | Solubility[1] | Thermal behavior[2] |
|---|---|---|---|---|---|
| 10 | 4 | 142.6 g = 77.5 | yellowish | total | 300° C. |
| 11 | 23 | 124.2 g = 67.5 | ocherous | abt. 85% | 280° C. |
| 12 | 42.5 | 119.1 g = 64.7 | light brown | abt. 75% | 270° C. |

[1] 1 g of substance must dissolve in 20 ml of hot water.
[2] Temperature where the poduct becomes black.

What is claimed is:

1. In a process for the manufacture of 7-nitro-1,3,5-triaza-adamantane by reaction of hexamethylene tetramine with nitromethane in an organic solvent at elevated temperature in the presence of an acid catalyst, the improvement which comprises using as solvent an aliphatic alcohol having from 1 to 4 carbon atoms and a water content not exceeding 4 weight %, or an anhydrous aliphatic monocarboxylic acid having from 1 to 3 carbon atoms, employing the catalyst in an amount at least equimolar to that of the hexamethylene tetramine, and carrying out the reaction at 40° to 180° C.

2. The process as claimed in claim 1, which comprises using equimolar amounts of hexamethylene tetramine and nitromethane.

3. The process as claimed in claim 1, wherein the organic solvent is methanol, ethanol or glacial acetic acid.

4. The process as claimed in claim 1, wherein the acid catalyst is an anhydrous aliphatic monocarboxylic acid having from 1 to 3 carbon atoms which simultaneously acts as solvent.

* * * * *

UNITED STATES PATENT AND TRADEMARK OFFICE
CERTIFICATE OF CORRECTION

PATENT NO. : 4,267,322
DATED : May 12, 1981
INVENTOR(S) : Hartmut Wiezer

It is certified that error appears in the above—identified patent and that said Letters Patent is hereby corrected as shown below:

Column 1, line 29, replace "hexamethylene triamine" by --hexamethylene tetramine--.

Col. 4, line 8 after "agitation" insert --in 250 ml of methanol--.

Signed and Sealed this

Sixth Day of October 1981

[SEAL]

Attest:

Attesting Officer

GERALD J. MOSSINGHOFF

Commissioner of Patents and Trademarks